US008956338B2

(12) United States Patent
Ichikawa et al.

(10) Patent No.: US 8,956,338 B2
(45) Date of Patent: **\*Feb. 17, 2015**

(54) WEARING ARTICLE WITH WAIST BELT MEMBER

(75) Inventors: Makoto Ichikawa, Kanonji (JP); Kenichi Sasayama, Kanonji (JP)

(73) Assignee: Uni-Charm Corporation, Ehime (JP)

( * ) Notice: Subject to any disclaimer, the term of this patent is extended or adjusted under 35 U.S.C. 154(b) by 708 days.
This patent is subject to a terminal disclaimer.

(21) Appl. No.: 13/260,855

(22) PCT Filed: Feb. 22, 2010

(86) PCT No.: PCT/JP2010/052595
§ 371 (c)(1),
(2), (4) Date: Sep. 28, 2011

(87) PCT Pub. No.: WO2010/113563
PCT Pub. Date: Oct. 7, 2010

(65) Prior Publication Data
US 2012/0035572 A1    Feb. 9, 2012

(30) Foreign Application Priority Data

Mar. 31, 2009 (JP) .................................. 2009-087195

(51) Int. Cl.
*A61F 13/15* (2006.01)
*A61F 13/49* (2006.01)
*A61F 13/496* (2006.01)

(52) U.S. Cl.
CPC ......... *A61F 13/49058* (2013.01); *A61F 13/496* (2013.01)
USPC ............................ 604/396; 604/387; 604/394

(58) Field of Classification Search
CPC ... A61F 13/49011; A61F 13/64; A61F 13/49; A61F 13/49061; A61F 13/49019; A61F 13/15609; A61F 13/49012; A61F 13/49015; A61F 13/4902; A61F 13/49017; A61F 13/15601; A61F 13/5633; A61F 13/49014; A61F 13/4906; A61F 13/49028; A61F 2013/51419

USPC .......... 604/385.01, 385.03, 385.11, 386–387, 604/392–393, 396–402
See application file for complete search history.

(56) References Cited

U.S. PATENT DOCUMENTS 5,607,416 A * 3/1997 Yamamoto et al. ........... 604/397
6,364,863 B1 * 4/2002 Yamamoto et al. ...... 604/385.27
(Continued)

FOREIGN PATENT DOCUMENTS

JP    2004-329238 A    11/2004
JP    2008-194161 A    8/2008
(Continued)

OTHER PUBLICATIONS

Supplementary European Search Report issued Jan. 9, 2014, corresponds to European patent application No. 10758340.3.
(Continued)

*Primary Examiner* — Michele M Kidwell
(74) *Attorney, Agent, or Firm* — Lowe Hauptman & Ham LLP (57) ABSTRACT

A wearing article has crotch-elastic elements extending in a longitudinal direction. Front and rear waist members and the crotch member are bonded one another by front and rear bonded regions. The front bonded region is contoured by first and second ends and both side edges obliquely extending in the longitudinal direction so as to intersect with the first and second ends and, outboard of the both side edges in a transverse direction, non-bonded regions in which the crotch member and the front waist member are not bonded to each other are defined. Front waist-elastic elements extend between both side edges of the front waist member. The crotch-elastic elements extend from a front end to a rear end of the crotch member in the longitudinal direction. In the front bonded region, the front waist-elastic elements and the crotch-elastic elements substantially intersect one another and interlock with one another.

7 Claims, 9 Drawing Sheets

(56) References Cited

U.S. PATENT DOCUMENTS

| | | | |
|---|---|---|---|
| 6,478,786 B1* | 11/2002 | Glaug et al. | 604/385.27 |
| 6,547,774 B2* | 4/2003 | Ono et al. | 604/385.29 |
| 6,755,808 B2* | 6/2004 | Balogh et al. | 604/385.28 |
| 7,195,622 B2* | 3/2007 | Lindstrom | 604/392 |
| 7,201,744 B2* | 4/2007 | Van Gompel et al. | 604/391 |
| 7,662,138 B2* | 2/2010 | Hermansson et al. | 604/396 |
| 7,815,620 B2* | 10/2010 | Coates et al. | 604/392 |
| 7,887,523 B2* | 2/2011 | Sasayama et al. | 604/385.09 |
| 7,955,311 B2* | 6/2011 | Tanaka et al. | 604/385.3 |
| 8,585,670 B2* | 11/2013 | Takino | 604/385.28 |
| 8,668,680 B2* | 3/2014 | Ichikawa et al. | 604/385.3 |
| 2005/0107763 A1* | 5/2005 | Matsuda et al. | 604/396 |
| 2005/0148965 A1 | 7/2005 | Richlen et al. | |
| 2012/0035572 A1* | 2/2012 | Ichikawa et al. | 604/385.3 |
| 2012/0259304 A1* | 10/2012 | Ichikawa et al. | 604/385.3 |
| 2012/0271266 A1* | 10/2012 | Sasayama et al. | 604/385.24 |
| 2013/0012905 A1* | 1/2013 | Katsuragawa et al. | 604/385.3 |
| 2013/0012907 A1* | 1/2013 | Sasayama et al. | 604/385.201 |
| 2013/0123735 A1* | 5/2013 | Ichikawa et al. | 604/385.19 |
| 2013/0123736 A1* | 5/2013 | Ichikawa et al. | 604/385.19 |
| 2013/0172841 A1* | 7/2013 | Ichikawa et al. | 604/366 |
| 2013/0184666 A1* | 7/2013 | Sasayama et al. | 604/378 |
| 2013/0226124 A1* | 8/2013 | Ichikawa et al. | 604/385.01 |
| 2013/0304011 A1* | 11/2013 | Sasayama et al. | 604/370 |
| 2013/0338623 A1* | 12/2013 | Kinoshita et al. | 604/385.29 |
| 2014/0031782 A1* | 1/2014 | Ichikawa et al. | 604/385.29 |
| 2014/0142531 A1* | 5/2014 | Sasayama et al. | 604/385.21 |

FOREIGN PATENT DOCUMENTS

| | | | | |
|---|---|---|---|---|
| JP | 2009-106666 A | | 5/2009 | |
| WO | 94/09736 | * | 5/1994 | A61F 13/15 |

OTHER PUBLICATIONS

International Search Report for PCT/JP2010/052595 mailed May 18, 2010.

* cited by examiner

WEARING ARTICLE WITH WAIST BELT MEMBER

RELATED APPLICATIONS

The present application is a National Phase of International Application Number PCT/JP2010/052595, filed Feb. 22, 2010 and claims priority from, Japanese Application Number 2009-087195, filed Mar. 31, 2009.

TECHNICAL FIELD

The present invention relates to wearing articles and more particularly to wearing articles such as disposable diapers, toilet-training pants or incontinent briefs.

BACKGROUND

A disposable diaper as one example of wearing articles including a waist belt member and a crotch member is known, for example, from JP 2008-194161 A (PTL 1). According to PTL 1, the diaper includes front and rear waist regions and a crotch region extending between these front and rear waist regions wherein the front and rear waist regions are defined by an outer tubular sheets and the crotch region is defined by an absorbent structure. Both ends of the absorbent structure are bonded to the outer tubular sheets by bonded regions, respectively. Each of the bonded regions includes a first bonded region formed almost over an entire area of the absorbent structure in a transverse direction and a second boned region being nearer the bottom of the diaper than the first bonded region and having a length dimension in the transverse direction smaller than that of the first bonded region. Outside both sides of the second bonded region in the transverse direction, the outer tubular sheet and the absorbent structure are not bonded one another. The arrangement that the outer tubular sheet and the absorbent structure are locally free from one another in this manner allows a contour length of each leg-opening defined by the outer tubular sheet and the absorbent structure to be enlarged so that the wearer's legs may be smoothly guided through the leg-openings.

CITATION LIST

Patent Literature

{PTL 1} JP 2008-194161 A

SUMMARY

Technical Problem

In this above-mentioned diaper, the outer tubular sheet and the absorbent structure are not bonded to one another outside the both side edges of the second bonded region and, as a result, the absorbent structure is readily deformed in such non-bonded region. Particularly in the vicinity of the wearer's thighs inclusive of inguinal regions, the absorbent structure is apt to be contracted in the transverse direction and an absorption area of this structure is correspondingly reduced. Eventually, the absorption capacity of the structure may be degraded until leakage of bodily fluids such as urine may occur. In addition, the contracted absorbent structure should be wedged in the wearer's bottom cleavage, leading to degradation of wear comfort and appearance.

An object of the present invention is to provide a wearing article improved so that leakage of bodily fluids can be reliably prevented without degradation of wear comfort and appearance.

Solution to Problem

According to the present invention, there is provided a wearing article having a longitudinal direction and a transverse direction including a skin-facing side, a non-skin-facing side, a front waist region, a rear waist region and a crotch region extending between the front and rear waist regions and further including a waist belt member defining the front and rear waist regions, a crotch member defining parts of the front and rear waist regions and the crotch region, a plurality of waist-elastic elements attached under tension to the waist belt member to extend in the transverse direction and a plurality of crotch-elastic elements attached under tension to the crotch member to extend in the longitudinal direction wherein the waist belt member includes a waist-side end extending in the transverse direction and defining a waist-opening and a leg-side end opposite to the waist-side end to define parts of respective leg-openings and wherein the crotch member includes a front end and a rear end extending in the transverse direction and both side edges extending in the longitudinal direction wherein the front end is bonded to the front waist region of the waist belt member via a front bonded region and the rear end is bonded to the rear waist region of the waist band member via a rear bonded region.

The present invention is characterized in that:

the front bonded region is formed on the non-skin facing side of the front waist region, non-bonded regions in which the front end of the crotch member and the waist belt member are not bonded to each other being formed outboard of both side edges of the front bonded region as viewed in the transverse direction and at least a part of the waist-elastic elements and at least parts of the crotch-elastic elements extend from the non-bonded regions to the front bonded region and the parts of the waist-elastic elements substantially intersect the parts of the crotch-elastic elements in the front bonded region. The term "substantially intersect" means that the waist-elastic elements and the crotch-elastic elements may be directly bonded to one another as well as may be indirectly bonded by means of other sheet member or the like.

According to one embodiment of the present invention, the waist-elastic elements are arranged to be spaced one from another in the longitudinal direction and the crotch-elastic elements are arranged to be spaced one from another in the transverse direction.

According to another embodiment, the waist-elastic elements include the inner-waist-elastic elements arranged on an inner side as viewed in the longitudinal direction and outer-waist-elastic elements arranged on an outer side as viewed in the longitudinal direction, the crotch-elastic elements include inner-crotch-elastic elements arranged on an inner side as viewed in the transverse direction and outer-crotch-elastic elements arranged on an outer side as viewed in the transverse direction, and the inner-waist-elastic elements substantially intersect with the inner-crotch-elastic elements and the outer-waist-elastic elements substantially intersect with the outer-crotch-elastic elements.

According to still another embodiment, the front bonded region is defined by a first end extending in the transverse direction, a second end opposed to the first end and extending in the transverse direction wherein the first end is nearer the waist-opening than the second end, and both side edges obliquely intersecting with the first and second ends and extending from the first end to the second end and substantially toward an imaginary longitudinal center line bisecting a length dimension in the transverse direction and the non-bonded regions are provided on outboard of the both side edges of the bonded region.

According to yet another embodiment, the rear bonded region lies on the non-skin-facing side of the rear waist region and formed over an entire area in which the rear end of the crotch member and the waist belt member overlap one another.

According to further another embodiment, the crotch member includes folding lines extending in the longitudinal direction and folded regions formed by folding the both side edges of the crotch member along the folding lines back toward the skin-facing side.

According to an alternative embodiment, the crotch-elastic elements are arranged at least in the folded regions.

Advantageous Effects of Invention

According to the present invention, the waist-elastic elements and the crotch-elastic elements substantially intersect one another in the front bonded region in which the waist member and the crotch member are bonded to each other. With this arrangement, the crotch-elastic elements for crotch member can move in response to contraction of the waist-elastic elements. Specifically, the crotch-elastic elements are pulled in the transverse direction as the waist-elastic elements contract in the transverse direction so that the crotch-elastic elements can be prevented from contracting in the transverse direction and thereby leakage of bodily fluids and degradation of wear comfort and appearance can be effectively restricted.

DESCRIPTION OF EMBODIMENTS

Embodiment 1

The present invention will be exemplarily described on the basis of a disposable diaper as one embodiment of the wearing article with reference to the accompanying drawings.

Figure 1:
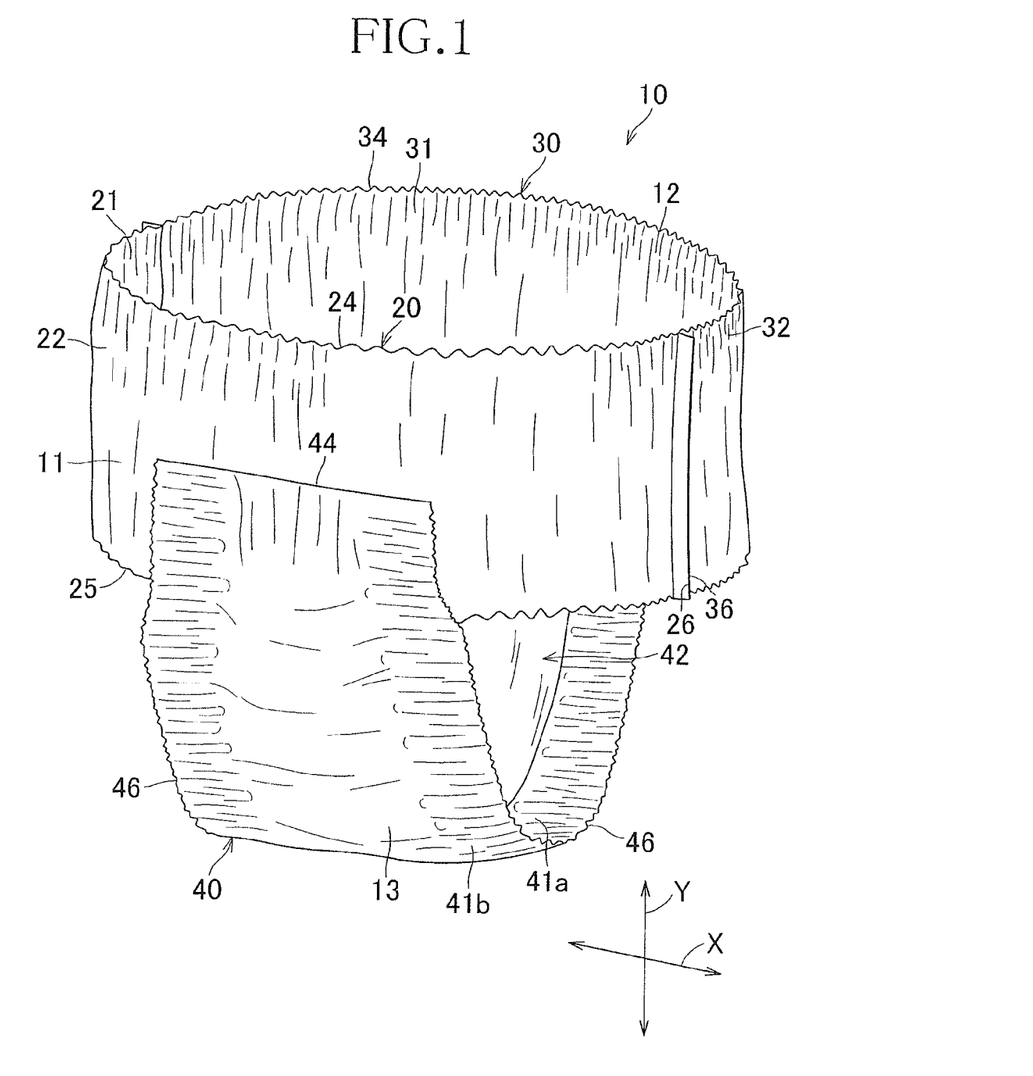
FIG. 1 A perspective view showing a disposable diaper as one example of wearing articles according to Embodiment 1.
Figure 2:
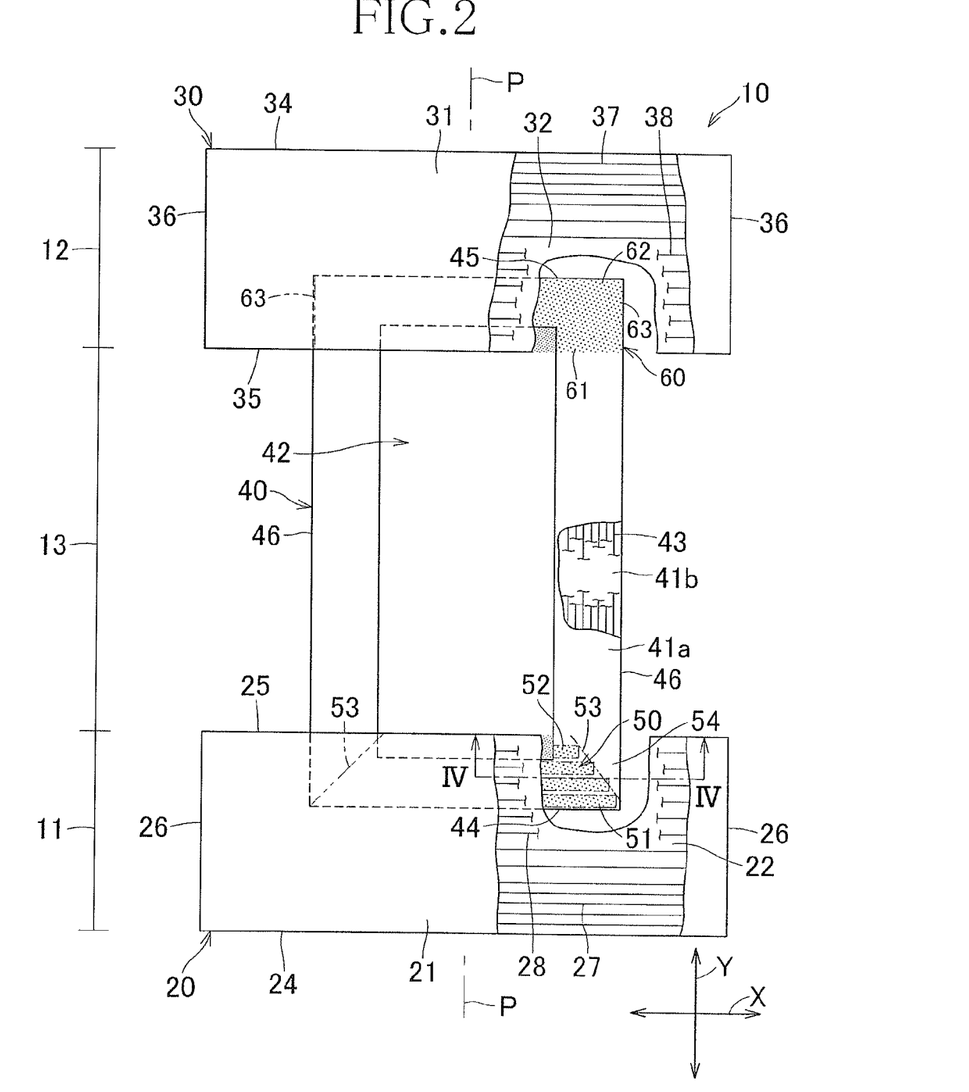
FIG. 2 A schematic plan view showing the diaper of FIG. 1 as has been flatly developed.
Figure 3:
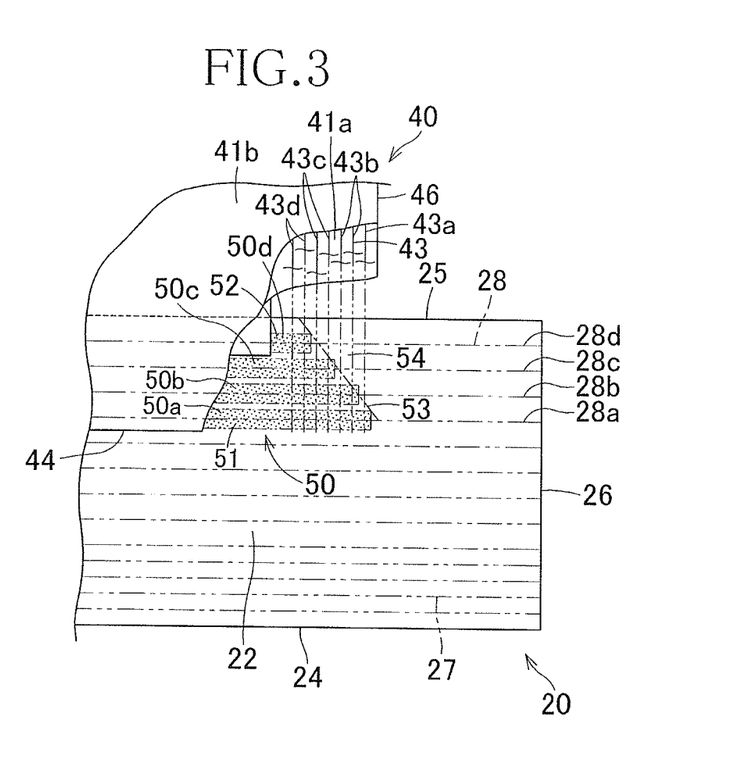
FIG. 3 A diagram schematically illustrating a part of FIG. 2.
Figure 4:
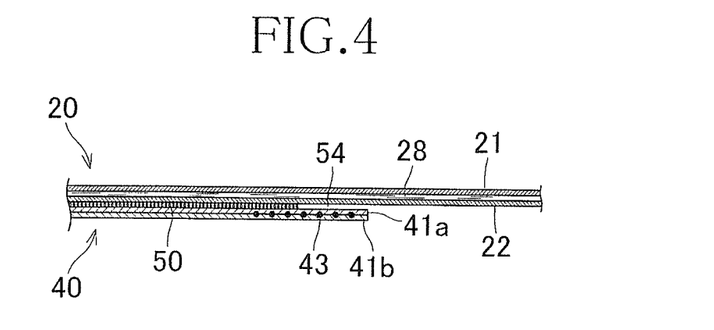
FIG. 4 A schematic sectional view taken along the line IV-IV in FIG. 2.

FIGS. 1 through 4 show Embodiment 1 as one of embodiments of the present invention. FIG. 1 is a perspective view showing the diaper 10 with its waist member kept in an annular state, FIG. 2 is a flatly developed plan view of the diaper 10 as viewed from its skin-facing side, FIG. 3 is a diagram schematically illustrating a part of FIG. 2 as viewed from its garment-facing side (i.e. non-skin-facing side) and FIG. 4 is a schematic sectional view taken along the line IV-IV in FIG. 2. FIGS. 2 and 3 are illustrated as partially broken away for convenience of illustration. FIGS. 2 through 4 illustrate the diaper 10 maintained flat by stretching respective elastic elements against contractile force thereof.

The diaper 10 has a longitudinal direction Y, a transverse direction X, an imaginary longitudinal center line P-P bisecting a length dimension of the diaper 10 in the transverse direction X, a skin-facing side and a garment-facing side and includes a front waist region 11, a rear waist region 12 and a crotch region 13 extending between these front and rear waist regions 11, 12 continuously in the longitudinal direction Y. The front waist region 11 is defined by a front waist member 20, the rear waist region 12 is defined by a rear waist member 30 and the crotch region 13 is defined by a crotch member 40. The diaper 10 is shaped symmetrically about the imaginary longitudinal center line P-P.

The front and rear waist members 20, 30 respectively include inner sheets 21, 31 defining the skin-facing side, outer sheets 22, 32 defining the side facing the garment facing side. A plurality of waist-elastic elements 27, 28 are sandwiched between the inner and outer sheets 21, 22 to be associated with the front waist member 20 and a plurality of elastic elements 37, 38 are sandwiched between the inner and outer sheets 31, 32 to be associated with the rear waist member 30. The front waist member 20 is contoured by an end 24 extending in the transverse direction X to define a front half of a waist-opening, an end 25 defining respective front halves of leg-openings and both side edges 26 extending in the longitudinal direction Y. In a similar fashion, the rear waist member 30 is contoured by an end 34 extending in the transverse direction X to define a rear half of the waist-opening, an end 35 defining respective rear halves of the respective leg-openings and both side edges 36 extending in the longitudinal direction Y. The side edges 26 of the front waist member 20 are joined to the side edges 36 of the rear waist member 30 to form an annular waist member.

The front waist member 20 includes the front waist-elastic element 27 attached thereto in the vicinity of the front waist-side end 24 defining the front half of the waist-opening and the front waist-elastic elements 28 attached thereto in the vicinity of the front leg-side end 25 defining respective front halves of the leg-openings. Each of the waist-elastic elements 27, 28 associated with the front waist member 20 is formed of a rubber thread and sandwiched under tension but in a contractible fashion between the inner and outer sheets 21, 22 and bonded to at least one of the inner and outer sheets 21, 22 with adhesives (not shown). In a similar manner, the rear waist member 30 includes rear waist-elastic elements 37 attached thereto in the vicinity of the rear waist-side end 34 defining the rear half of the waist-opening and rear waist-elastic elements 38 in the vicinity of the rear leg-side end 35 defining respective rear halves of the leg-openings. Each of the elastic elements 37, 38 associated with the rear waist member 30 is formed of a rubber thread and sandwiched under tension but in a contractible fashion between the inner and outer sheets 31, 32 and bonded to at least one of the inner and outer sheets 31, 32 with adhesives (not shown).

The front and rear waist members 20, 30 are elasticized in the transverse direction X under the effect of the associated waist-elastic elements 27, 28, 37, 38. In the front and rear waist-elastic elements 27, 37, each pair of the adjacent elastic elements may be spaced by a distance in a range of about 3 to 8 mm in the longitudinal direction Y. In the front and rear waist-elastic elements 28, 38, each pair of the adjacent elastic elements may be spaced by a distance in a range of about 8 to 20 mm. By arranging a distance between each adjacent pair of the front and rear waist-elastic elements 27, 37 at a relatively small pitch, the diaper 10 can be prevented from slipping down along the wearer's waist. By arranging a distance between each adjacent pair of the front and rear waist-elastic elements 28, 38 at a relatively large pitch, a tensile stress in a region defined below the waist-opening can be reduced to assure such region defined below the waist-opening to come in not excessively but moderately close contact with the wearer's body without a gap left between the lower region of the diaper and the wearer's body which should cause leakage of bodily fluids. It should be appreciated that the adjustable variation of the tensile stress can be achieved not only by varying the pitch of the elastic elements in the longitudinal direction but also by the other measures such as variation of thickness or load for stretching of the elastic elements.

The crotch member 40 includes liquid-impervious inner and outer sheets 41a, 41b exclusively for the crotch member 40, a liquid-absorbent structure 42 lying on the skin-facing side of the inner sheet 41a and a plurality of crotch-elastic elements 43 arranged outside the liquid-absorbent structure 42 as viewed in the transverse direction X wherein the crotch member 40 is integrally formed by these components. The crotch member 40 is contoured by a front end 44 and a rear end 45 each extending in the transverse direction X and both side edges 46 extending in the longitudinal direction Y. The inner sheet 41a is bonded along the front and rear ends 44, 45 to the outer sheets 22, 32 of the front and rear waist members 20, 30, respectively. In this way, the diaper 10 is pant-shaped as a whole.

The crotch-elastic elements 43 extend along the both side edges 46 in the longitudinal direction Y and are attached under tension but in a contractible fashion between the inner and outer sheets 41a, 41b. Each of the crotch-elastic elements 43 is formed of a rubber thread and spaced one from another at a pitch of about 5 to 20 mm in the transverse direction X. The crotch-elastic elements 43 serve to elasticize the crotch member 40 in the longitudinal direction Y.

The crotch member 40 is bonded to the front and rear waist members 20, 30 via front and rear bonded regions 50, 60. The front bonded region 50 includes a first sub-region 50a being near the front waist-side end 24, a second sub-region 50b being nearer the front leg-side end 25 than the first sub-region 50a and having a length dimension in the transverse direction X smaller than that of the first sub-region 50a, a third sub-region 50c being nearer the front leg-side end 25 than the second sub-region 50b and having a length dimension in the transverse direction smaller than that of the second sub-region 50b and a fourth sub-region 50d being nearer the front leg-side end 25 than the third sub-region 50c and having a length dimension in the transverse direction X smaller than that of the third sub-region 50c. From the front waist-side end 24 the front leg-side end 25, respective transversely side edges of these first through fourth sub-regions 50a through 50d stepwise shift inwardly as viewed in the transverse direction X, in other words, toward the imaginary longitudinal center line P-P.

The front bonded region 50 has a first end 51 extending in the transverse direction X and being near the front waist-side end 24 on the first sub-region 50a and a second end 52 extending in the transverse direction X and being near the front leg-side end 25 on the fourth sub-region 50d. Both of the transversely side edges of the first through fourth sub-regions 50a through 50d respectively opposite in the transverse direction X define both side edges 53 of the front bonded region 50 obliquely extending in the longitudinal direction Y substantially across the first and second ends 51, 52. More specifically, the transversely side edges of the first through fourth sub-regions 50a through 50d are connected to one another and defining the above-mentioned side edges 53 which are substantially straight lines. In this way, the first and second ends 51, 52 cooperate with the both side edges 53 to define the front bonded region 50 of a substantially trapezoidal shape being relatively long in the transverse direction X. From the viewpoint of a positional relationship, the first end 51 substantially coincides with the front end 44 of the crotch member 40 and the second end 52 substantially coincides with the front leg-side end 25. In the front bonded region 50 formed of hot melt adhesives or the like, preferably the first and second ends 51, 52 should not extend outward from the front end 44 of the crotch member 40 and the front leg-side end 25 or else the adhesives might run off beyond the region 50 and uncomfortably irritate the wearer's skin.

Outside the both side edges 53 as viewed in the transverse direction X, non-bonded regions 54 in which the crotch member 40 and the front waist member 20 are not bonded to each other is defined. Specifically, each of these non-bonded regions 54 is indicated by a triangular region contoured by the side edge 53, the associated side edge 46 of the crotch member 40 and the front leg-side end 25. The terms "substantially straight", "substantially trapezoidal" and "substantially triangular" used herein describing about the both side edges 53, the front bonded region 50 and the non-bonded regions respectively mean inclusively, when describing strictly, those have the side edge 53 extending in stepwise fashion as shown in the front bonded region 50 of FIG. 2 having the length dimension in the transverse direction X stepwise shortened.

The front waist-elastic elements 28 extend fully between the both side edges 26 of the front waist member 20 in the transverse direction X. More specifically, the front waist-elastic elements 28 continuously extend in the transverse direction X across one of the non-bonded regions 54, the front bonded region 50 and the other of the non-bonded regions 54. The first through fourth front waist-elastic elements 28a through 28d which are included in the front waist-elastic elements 28 are respectively allotted to the first through fourth sub-regions 50a through 50d of the front bonded region 50 wherein the first and second elastic elements 28a, 28b define an "outer side front waist-elastic element" and the third and fourth elastic elements 28c, 28d define an "inner side front waist-elastic element" both as viewed in the longitudinal direction Y.

The crotch-elastic elements 43 continuously extend in the longitudinal direction from the front end 44 of the crotch member 40 to the rear end 45 of the crotch member 40 across the non-bonded regions 54 and then the front bonded region 50. Each of the crotch-elastic elements 43 includes a first crotch-elastic element 43a arranged outermost in the transverse direction X, two second crotch-elastic elements 43b arranged inside the first crotch-elastic element 43a in the transverse direction X, two third crotch-elastic elements 43c arranged inside the second crotch-elastic elements 43b and two fourth crotch-elastic elements 43d arranged inside the third crotch-elastic elements 43c in the transverse direction X. The first and second crotch-elastic elements 43a, 43b define an "outer side crotch-elastic element" and third and fourth crotch-elastic elements 43c, 43d define "inner side crotch-elastic element" both as viewed in the transverse direction X.

In each of the non-bonded regions 54, the first through fourth front waist-elastic elements 28a through 28d and the first through fourth crotch-elastic elements 43a through 43d for the crotch member 40 merely and indirectly overlap each other in the thickness direction of the front and rear waist members 20, 30 or the crotch member 40 via the outer sheet 22 of the front waist member 20 and the inner sheet 41a of the crotch member 40. Contrastingly, in the front bonded region 50, the front waist-elastic elements 28 substantially intersect and are interlocked with the crotch-elastic elements 43 as the outer sheet 22 of the front waist member 20 and the inner sheet 41a of the crotch member 40 are bonded to each other. More specifically, the first front waist-elastic elements 28a substantially intersects with the first crotch-elastic element 43a in the first sub-region 50a, the second front waist-elastic elements 28b substantially intersects with the second crotch-elastic elements 43b in the second sub-region 50b, the third front waist-elastic elements 28c substantially intersects with the third crotch-elastic elements 43c in the third sub-region 50c and the fourth front waist-elastic elements 28d substantially intersects with the fourth crotch-elastic elements 43c in the fourth sub-region 50d.

The expression "substantially intersect with" used herein means inclusively that, even when the front waist-elastic elements 28 are contiguous via the outer sheet 22 of the front waist member 20 and the inner sheet 41a of the crotch member 40, i.e., indirectly, to the crotch-elastic elements 43 as this Embodiment 1 is the case, wherein the front waist-elastic elements 28, and the crotch-elastic element 43 can be considered to be substantially in the same relationship as the relationship in which the front waist-elastic elements 28, and the crotch-elastic element 43 directly intersect with each other so far as the front waist-elastic elements 28, and the crotch-elastic element 43 are interlocked with each other. Description given hereunder relating to intersection of the front waist-elastic elements 28, and the crotch-elastic element 43 should be construed in this meaning.

As previously described, the front bonded region 50 is defined in the substantially trapezoidal shape which is relatively long in the transverse direction X as shown by FIG. 2 and each of the non-bonded regions 54 is defined substantially in the triangular shape. However, the essential feature of the present invention lies in that the non-bonded regions 54 are defined on both side edges 53 of the front bonded region 50 immediately outside the side edges 53 of the front bonded region 50. In view of this, an alternative arrangement is possible without departing from the scope of the invention such that the bonded region is not formed in almost entire area between the both side edges 53 but a pair of bonded regions is defined in the vicinity of intersections between the front end 44 of the crotch member 40 and the side edges 46 of the crotch member 40 so as to be spaced from each other, for example, each in a substantially triangular shape similar to the shape of the non-bonded region 54. It should be appreciated here that preferably the both side edges 53 not only intersect with the first and second ends 51, 52 but also these side edges 53 obliquely extend toward the second end 52 and the imaginary longitudinal center line P-P.

The front waist-elastic elements 28 are interlocked with the crotch-elastic elements 43 so that the crotch-elastic elements 43 also may be stretched outward n the transverse direction X as the front waist-elastic elements 28 are stretched outward in the transverse direction X. The crotch member 40 is free from the front waist member 20 in the non-bonded regions 54 and correspondingly facilitated to move in the transverse direction X. However, the both side edges 46 of the crotch member 40 provided with the crotch-elastic elements 43 can be pulled outward in the transverse direction X by stretching the front waist-elastic elements 28 and thereby the crotch member can be prevented from being gathered inward. Consequentially, the effective area of the liquid-absorbent structure 42 would not be reduced, leading to leakage of bodily fluids such as urine. In addition, the crotch member 40 should not be wedged in the wearer's bottom cleavage and thereby the feeling to wear as well as the appearance of the diaper would not be deteriorated.

The crotch-elastic elements 43 are bonded to the front waist-elastic elements 28 along the side edges 53 of the bonded region 50 so that the first through fourth crotch-elastic elements 43a through 43d may be bonded to the first through fourth front waist-elastic elements 28a-28d, respectively. In this way, the both side edges 46 of the crotch member 40 can be pulled outward in the transverse direction X in a correspondingly larger range.

Theoretically, sum of contractile force of the front waist-elastic elements 28 acting between the respective side edges 26 of the front waist member 20 and the respective side edges 53 of the front bonded region 50 plus contractile force of the crotch-elastic elements 43 acting between the respective side edges 53 of the front bonded region 50 and the rear end 45 of the crotch member 40 serves to pull the crotch member 40 upward. With such unique arrangement, it is assured that the contractile force of the front waist-elastic elements 28 is almost evenly allotted to the first through fourth front waist-elastic elements 28a through 28d and the contractile force of the crotch-elastic elements 43 is also almost evenly allotted to the first through fourth crotch-elastic elements 43a-43d. As a consequence, the effect of these elastic members should not be locally enhanced. In this way, uncomfortable local oppressive feeling otherwise experienced by the wearer can be reliably restricted to provide even and comfortable fitness.

The non-bonded regions 54 are provided between the crotch member 40 and the front waist member 20 allow the leg-openings defined by the front leg-side end 25, the rear leg-side end 35 and the both side edges 46 of the crotch member 40 to be broadened in the course of putting the diaper 10 on the wearer's body and thereby facilitate the diaper 10 to be smoothly put on.

The crotch member 40 is bonded also to the rear waist member 30 wherein the inner sheet 41a of the crotch member 40 is bonded to the rear waist member 30 in a rear bonded region 60. The rear bonded region 60 is contoured by a third end 61 extending in the transverse direction X almost in coincidence with the rear leg-side end 35, a fourth end 62 extending in the transverse direction X almost in coincidence with the rear end 45 of the crotch member 40 and both side edges 63 extending in the longitudinal direction Y. In the rear bonded region 60 formed of hot melt adhesives, preferably the third and fourth ends 61, 62 should not extend outward from the rear end 45 of the crotch member 40 and the rear leg-side end 35 or else the adhesives might run off beyond the region 50 and uncomfortably irritate the wearer's skin, as has been described with respect to the front bonded region 50.

The third end 61 and the fourth end 62 have substantially same length dimension in the transverse direction X and cooperate with the both side edges 63 to define a rectangular region which is relatively long in the transverse direction X. In this manner, the rear bonded region 60 serves to bond the rear end 45 of the crotch member 40 over the entire area of the above rectangular region to the rear waist member 30. In other words, the transverse direction X of the crotch member 40 can be surely fixed to the rear waist member 12 so that the crotch member 40 may be prevented from contraction in the transverse direction X and come in contact with the wearer's skin over an area as wide as possible.

While the crotch member 40 is bonded preferably to the outer sheet 32 of the rear waist member 30 when the crotch member 40 is bonded to the rear waist member 30 in the case in which the crotch member 40 is bonded to the front waist member 20, it is also possible to bond the crotch member 40 to the inner sheet 31 of the rear waist member 30, if desired.

The liquid-absorbent structure 42 may be bonded over its entire area to the inner sheet 41a of the crotch member 40. In another embodiment, the liquid-absorbent structure 42 can be partially bonded to the inner sheet 41a to leave gaps between the inner sheet 41a and the liquid-absorbent structure 42 so that the liquid-absorbent structure 42 can absorb bodily fluids such as urine through its upper and lower surfaces. As still another alternative arrangement, it is also possible to bond the crotch member 40 to the front and rear waist members 20, so that the front and rear ends of the liquid-absorbent structure 42 may coincide with the front waist end 25 and the rear waist end 35.

The front and rear bonded regions 50, 60 may be formed of adhesives but not limited thereto and the other means conventionally used in the relevant technical field such as thermal bonding or ultrasonic bonding may be used to form these bonded regions 50, 60. Furthermore, it is possible to form non-bonded regions also in combination with the rear bonded region 60 like the front non-bonded regions in combination with the front bonded regions 50. In this case, the rear waist-elastic elements of the rear waist member may intersect with the crotch-elastic elements in the rear bonded region.

The inner and outer sheets 41a, 41b of the crotch member 40 may be formed of liquid-impervious film or fibrous non-woven fabric or a laminate thereof. As the liquid-absorbent structure, for example, a mixture of liquid-absorbent core and super-absorbent polymer particles wrapped with a liquid-dispersant sheet may be used.

Embodiment 2

Figure 5:
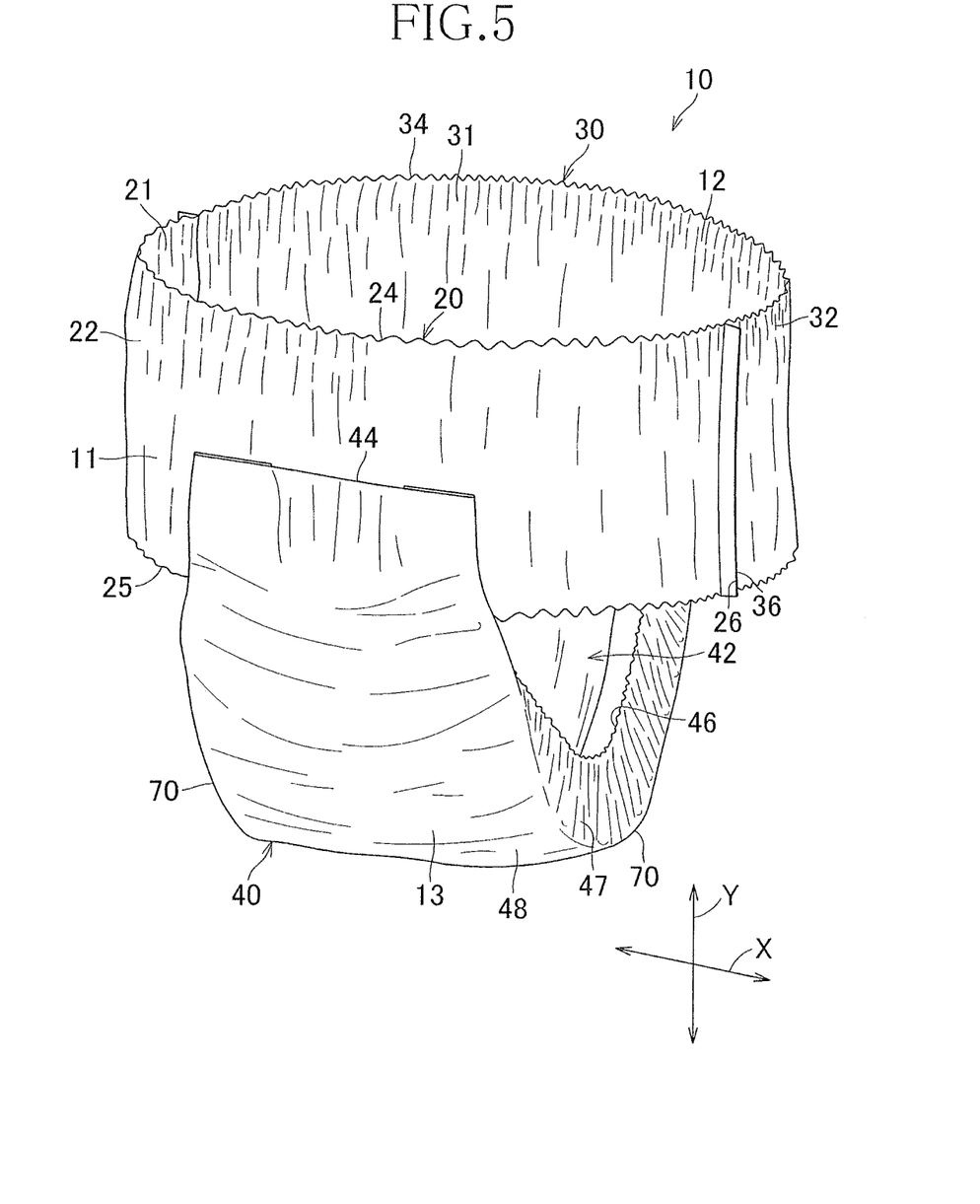
FIG. 5 A perspective view showing the diaper according to Embodiment 2.
Figure 6:
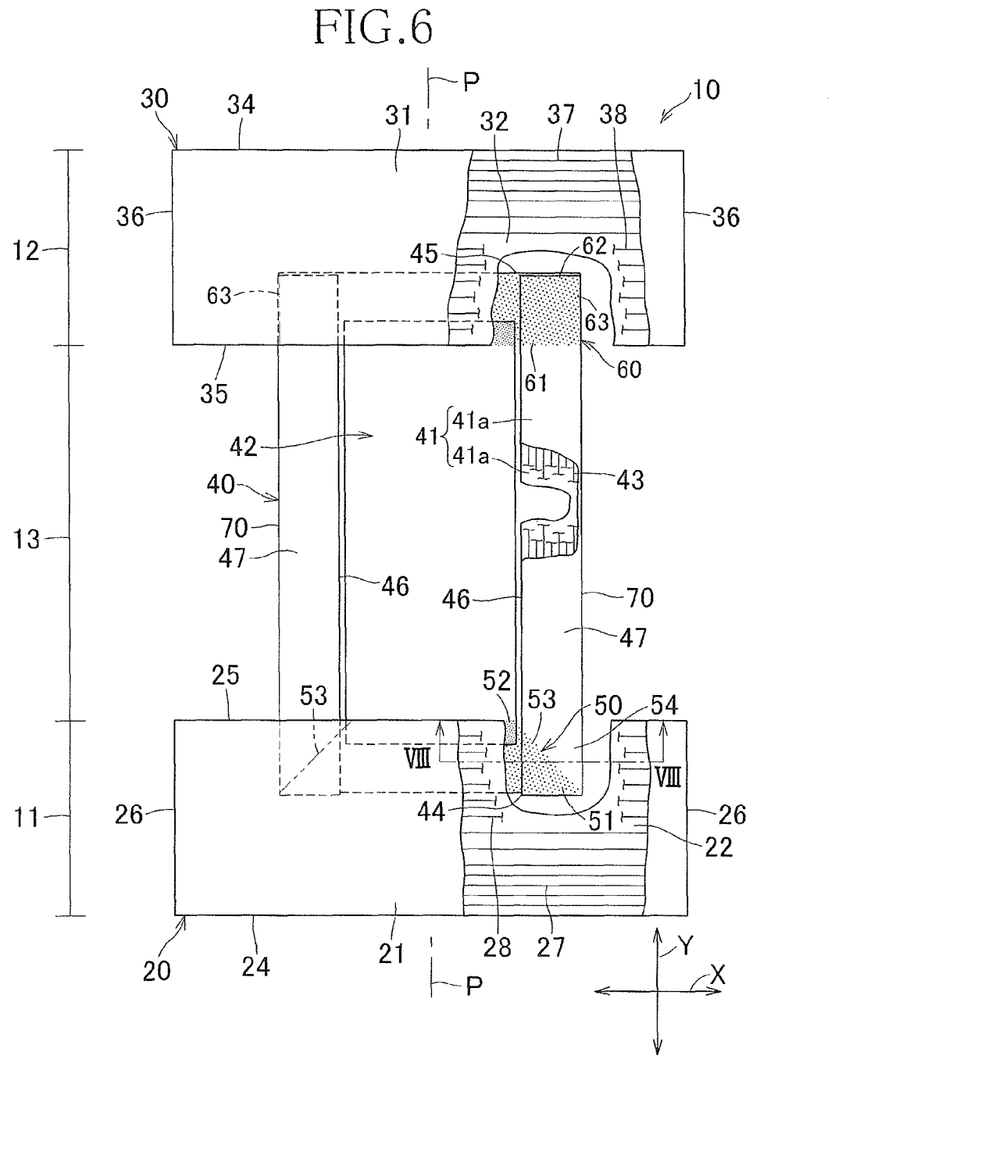
FIG. 6 A plan view showing the diaper of FIG. 5 as has been flatly developed.
Figure 7:
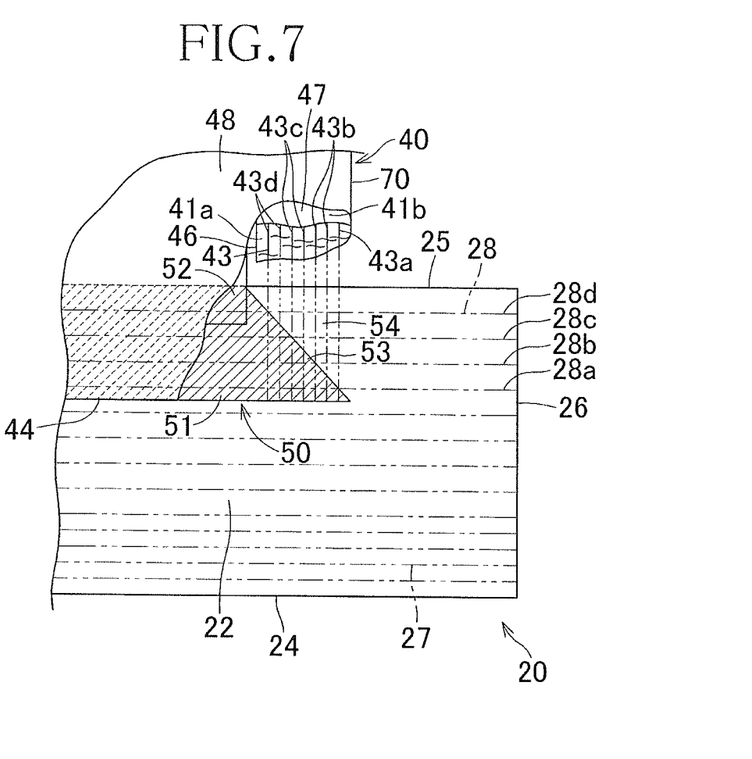
FIG. 7 A diagram schematically illustrating a part of FIG. 6.
Figure 8:
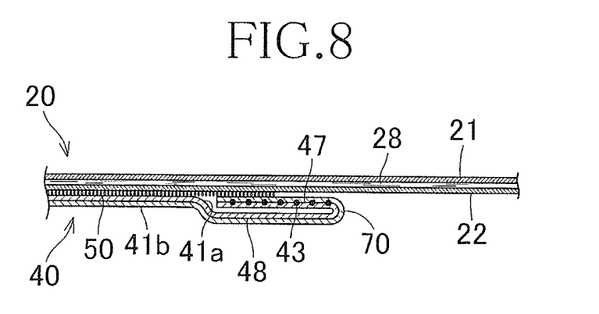
FIG. 8 A schematic sectional view taken along the line VIII-VIII in FIG. 6.

FIGS. 5 through 8 illustrate Embodiment 2 as another embodiment of the present invention wherein FIG. 5 shows the diaper 10 according to Embodiment 2 in a perspective view with a waist member maintained in an annular state, FIG. 6 is a flatly developed plan view of the diaper 10 as viewed from its side facing the wearer's body, FIG. 7 is a diagram schematically illustrating a part of FIG. 6 as viewed from its garment-facing side and FIG. 8 is a schematic sectional view taken along the line VIII-VIII in FIG. 6. FIGS. 6 and 7 are illustrated as partially broken away for convenience of illustration. FIGS. 6 through 8 illustrate the diaper 10 maintained flat by stretching respective elastic elements against contractile force thereof.

With respect to the components in this Embodiment 2 similar to those in Embodiment 1, description in detail will be eliminated.

Embodiment 2 is characterized in that the crotch member 40 is formed with folding lines 70 extending in the longitudinal direction Y along which the both side edges 46 of the crotch member 40 are folded inward and the both side edges 53 of the front bonded region 50 obliquely extend in form of continuous straight lines. The crotch member 40 is provided between the folding lines 70 and the associated side edges 46 of the crotch member 40, respectively, the elastic elements 43 each of which is formed of a rubber thread. The both side edges 46 of the crotch member 40 are folded back toward the skin-facing side so as to define folded regions 47 and a crotch member's main body 48. In vicinities of the front and rear ends 44, 45 of the crotch member 40, opposite halves of the respective folded regions 47 regions are bonded together via the inner sheet 41a and, along the intermediate segments, opposite halves of the respective folded regions are not bonded together (not shown). With such arrangement, the intermediate segments of the respective folded regions 47 are spaced from the crotch member's main body 48 to raise themselves toward the wearer's skin under contractile force of the elastic elements 43 for the crotch member 40 and function as leakage barrier cuffs against leakage of bodily fluids such as urine. It should be understood that, in the front and rear waist regions 11, 12, the front and rear waist members 20, 30 interfere with formation of such barrier cuffs by the folded regions 47. In other words, the folded regions 47 can form the barrier cuffs exclusively in the crotch region 13.

The folded regions 47 are formed on both sides of the front bonded region 50 as viewed in the transverse direction X and the crotch member's main body 48 is defined between these folded regions 47. In the respective folded regions 47, the first through fourth front waist-elastic elements 28a through 28d intersect with the first through fourth crotch-elastic elements 43a through 43d for the crotch member 40. As a consequence, contractile force of the first through fourth front waist-elastic elements 28a through 28d can serve to pull the crotch member 40 outward in the transverse direction X and simultaneously to space the folded regions 47 from the crotch member's main body 48. In this manner, the reliable leakage-preventing function can be assured.

Embodiment 3

Figure 9:
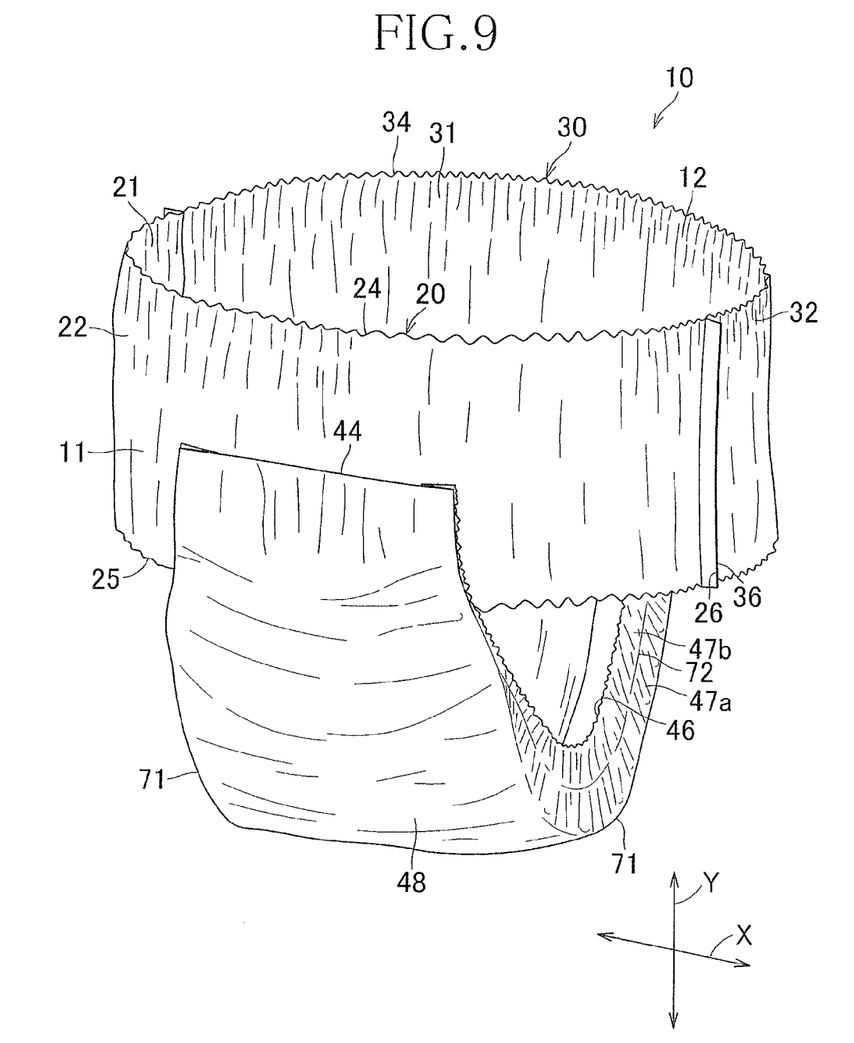
FIG. 9 A perspective view showing the diaper according to Embodiment 3.
Figure 10:
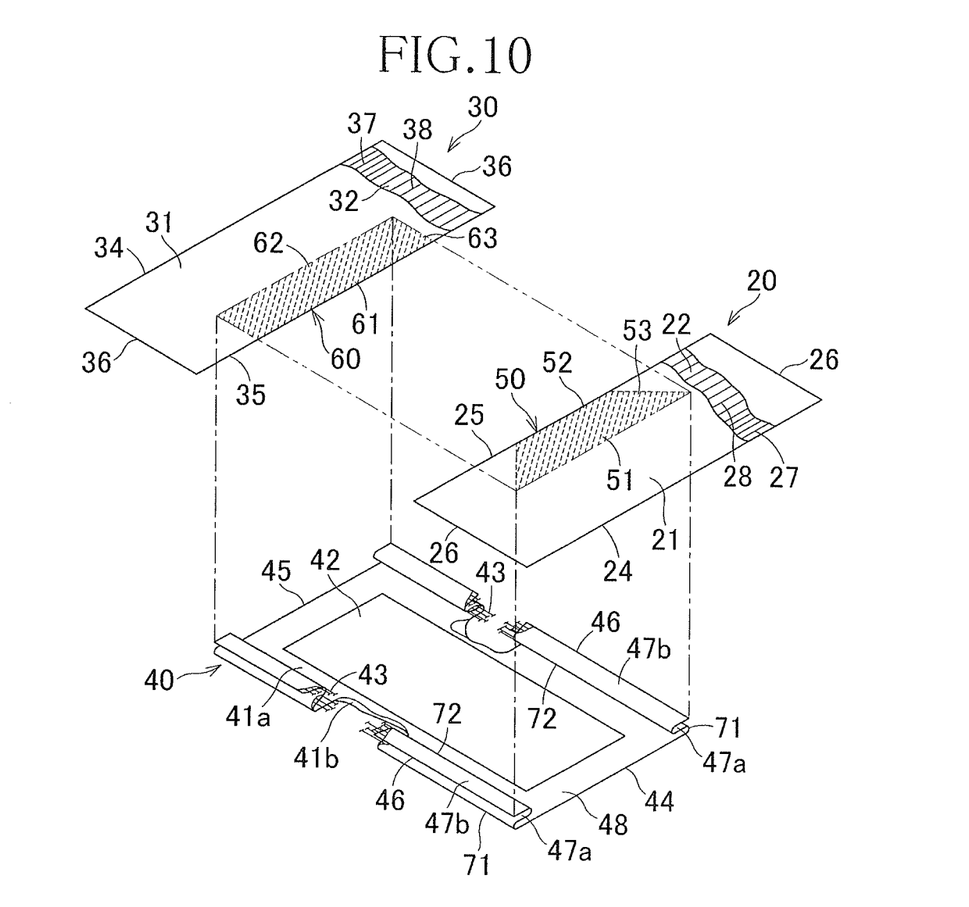
FIG. 10 An exploded view corresponding to the flatly developed plan view of FIG. 9.
Figure 11:
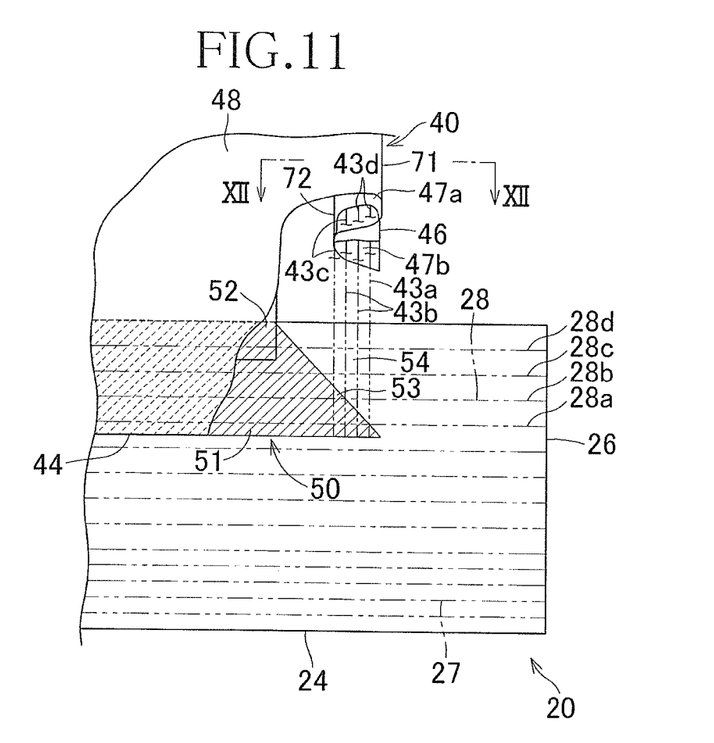
FIG. 11 A diagram schematically illustrating a part of FIG. 10.
Figure 12:
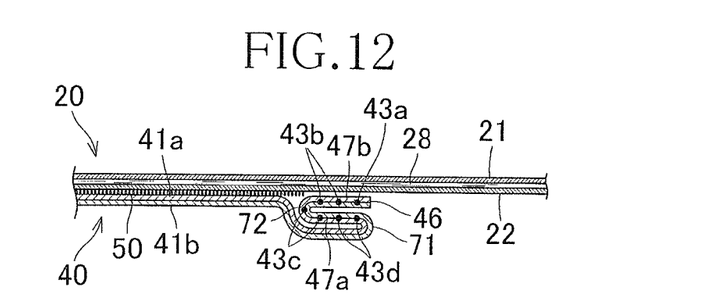
FIG. 12 A schematic sectional view taken along the line XII-XII in FIG. 11.

FIGS. 9 through 12 illustrate Embodiment 3 as still another embodiment of the present invention. FIG. 9 shows the diaper 10 according to Embodiment 3 in a perspective view with a waist member maintained in an annular state, FIG. 10 is a exploded view of the flatly developed diaper 10 of FIG. 9 as viewed from its skin-facing side, FIG. 11 is a diagram schematically illustrating a part of FIG. 10 as viewed from its garment-facing side and FIG. 12 is a schematic sectional view taken along the line XII-XII in FIG. 11. FIGS. 10 and 11 are illustrated as partially broken away for convenience of illustration. FIGS. 10 through 12 illustrate the diaper 10 maintained flat by stretching respective elastic element against contractile force thereof.

Regarding the components in this Embodiment 3 similar to those in Embodiment 1, description in detail will be eliminated.

Embodiment 3 is characterized in that the crotch member 40 is formed with first and second folding lines 71, 72 extending in the longitudinal direction Y along which the both side edges of the crotch member 40 are folded back. Embodiment 3 is characterized also in that the both side edges 53 of the front bonded region 50 obliquely and continuously extend in the form of straight lines.

The first and second folding lines 71, 72 are arranged to extend substantially in parallel to each other wherein each of the second folding lines 72 is placed nearer the associated side edge 46 of the crotch region than the associated first folding line 71. The crotch member 40 includes a pair of first folded regions 47a respectively defined between the first folding lines 71 and the associated second folding lines 72, a pair of second folded regions 47b defined between the second folding lines 72 and the associated side edges 46 of the crotch member 40 and the crotch member's main body 48 defined between the first folding lines 71. The second folded regions 47b lie on the side facing the front waist member 20, i.e., on the skin-facing side and the first folded regions 47a lie on the side facing the crotch member's main body 48, i.e., on the garment-facing side.

At the front and rear ends 44, 45 of the crotch member 40, the first folded regions 47a and the associated second folded regions 47b are bonded together via the opposed sections of the outer sheet 41b and the first folded regions 47a are bonded to the crotch member's main body 48 via the opposed sections of the inner sheet 41a (not shown).

The first and second folded regions 47a, 47b are respectively provided with the elastic elements 43 each of which is formed of a rubber thread for the crotch member 40.

The front bonded region 50 is formed outside of the second folding lines 72 as viewed in the transverse direction X in the second folded regions 47b and between the second folded lines 72 on the crotch member's main body 48. In the second folded regions 47b, the first and second front waist-elastic elements 28a, 28b intersect with the first and second crotch-elastic elements 43a, 43b so that the second folded regions 47b may be pulled outward in the transverse direction X under contractile force of the first and second front waist-elastic elements 28a, 28b and, in response to this, the first folded regions 48a also may be pulled outward. It is assured thus that the first and second folded regions 47a, 47b can be spaced upward from the crotch member's main body 48 to achieve the leakage-preventing function. The crotch member 40 is pulled outward in the transverse direction X under contractile force of the front waist-elastic elements 28 in the same manner as occurring in the Embodiments 1 and 2.

According to this Embodiment 3, in addition to the first folded regions 47a, the second folded regions 47b are formed to enlarge a total area of these folded regions and thereby to improve the barrier effect against leak of bodily fluids such as urine.

The various features of the invention such as the number of the folding lines and the arrangement of the elastic elements for the crotch member are not limited to those indicated and described in the respective Embodiments 1, 2 and 3, but may be appropriately modified. While these Embodiments 1, 2 and 3 have been described above on the basis of so-called pants-type or pull on-type diaper, the present invention is applicable also to so-called open-type diaper.

While a plurality of elastic elements are used in these Embodiments as the elastic elements for the waist members and the crotch member, it is also possible to use elastic bands or elasticized non-woven fabric as these elastic elements. These elastic elements for the waist members and the crotch member may be arranged so that these elastic elements at least partially intersect one with another in the front bonded region 50 to assure that contractile force of the elastic elements for the waist members in the transverse direction X can be transmitted to the elastic elements for the crotch member and thereby contraction of the elastic elements for the crotch member 40 in the transverse direction X can be restricted.

REFERENCE SIGNS LIST 10 diaper (wearing article)
11 front waist region
12 rear waist region
13 crotch region
20 front waist member
24 front waist-side end
25 front leg-side end
28 front waist-elastic element
30 rear waist member
34 rear waist-side end
35 rear leg-side end
38 rear waist-elastic element
40 crotch member
43 crotch-elastic element
44 front end of crotch member
45 rear end of crotch member
46 side edges of crotch member
47 folded regions
47a first folded regions
47b second folded regions
50 front bonded region
51 first end
52 second end
53 front side edges
54 non-bonded regions
60 rear bonded region
70 folding lines
71 first folding line
72 second folding line

The invention claimed is:

1. A wearing article having a longitudinal direction, a transverse direction, a skin-facing side, and a non-skin-facing side, said wearing article comprising:
a front waist region, a rear waist region and a crotch region extending between the front and rear waist regions,
a waist belt member defining the front and rear waist regions,
a crotch member defining parts of the front and rear waist regions and the crotch region,
a plurality of waist-elastic elements attached under tension to the waist belt member to extend in the transverse direction, and
a plurality of crotch-elastic elements attached under tension to the crotch member to extend in the longitudinal direction,
wherein
the waist belt member includes a waist-side end extending in the transverse direction and defining a waist-opening and a leg-side end opposite to the waist-side end to define parts of respective leg-openings,
the crotch member includes a front end and a rear end extending in the transverse direction and both side edges extending in the longitudinal direction, wherein the front end is bonded to the front waist region of the waist belt member via a front bonded region and the rear end is bonded to the rear waist region of the waist band member via a rear bonded region,
the front bonded region is formed on the non-skin-facing side of the front waist region,
non-bonded regions in which the front end of the crotch member and the waist belt member are not bonded to each other are formed outboard of both side edges of the front bonded region as viewed in the transverse direction, and
at least parts of the waist-elastic elements and at least parts of the crotch-elastic elements extend from the non-bonded regions to the front bonded region and the parts of the waist-elastic elements substantially intersect the parts of the crotch-elastic elements in the front bonded region.

2. The wearing article defined by claim 1, wherein the plurality of waist-elastic elements are arranged to be spaced one from another in the longitudinal direction and the plurality of crotch-elastic elements are arranged to be spaced one from another in the transverse direction.

3. The wearing article defined by claim 2, wherein:
the waist-elastic elements include inner side-waist-elastic elements arranged on an inner side as viewed in the longitudinal direction and outer side-waist-elastic elements arranged on an outer side as viewed in the longitudinal direction,
the crotch-elastic elements include inner-crotch-elastic elements arranged on an inner side as viewed in the transverse direction and outer-crotch-side elastic elements arranged on an outer side as viewed in the transverse direction, and
the inner side-waist-elastic elements substantially intersect with the inner-crotch-elastic elements and the outer side-waist-elastic elements substantially intersect with the outer-crotch-elastic elements for the crotch member.

4. The wearing article defined by claim 1, wherein:
the front bonded region is defined by a first end extending in the transverse direction, a second end opposed to the first end and extending in the transverse direction, wherein the first end is nearer the waist-opening than the second end, and the both side edges of the front bonded region obliquely intersecting with the first and second ends and extending from the first end to the second end and substantially toward an imaginary longitudinal center line bisecting a length dimension in the transverse direction, and
the non-bonded regions are provided on outboard of the both side edges of the front bonded region.

5. The wearing article defined by claim 1, wherein the rear bonded region lies on the non-skin-facing side and formed over an entire area in which the rear end of the crotch member and the waist belt member overlap one another.

6. The wearing article defined by claim 1, wherein the crotch member comprises folding lines extending in the longitudinal direction and folded regions formed by folding the both side edges of the crotch member along associated the folding lines back toward the skin-facing side.

7. The wearing article defined by claim 6, wherein the crotch-elastic elements are arranged at least in the folded regions.

\* \* \* \* \*